United States Patent
Purves et al.

(10) Patent No.: US 11,035,789 B2
(45) Date of Patent: Jun. 15, 2021

(54) CAVITY RING-DOWN SPECTROSCOPY SYSTEM AND METHOD OF MODULATING A LIGHT BEAM THEREIN

(71) Applicant: Picomole Inc., Moncton (CA)

(72) Inventors: Christopher Quentin Purves, Moncton (CA); Denis Dufour, Montreal (CA)

(73) Assignee: PICOMOLE INC., Moncton (CA)

( * ) Notice: Subject to any disclaimer, the term of this patent is extended or adjusted under 35 U.S.C. 154(b) by 0 days.

(21) Appl. No.: 16/509,207

(22) Filed: Jul. 11, 2019

(65) Prior Publication Data

US 2020/0319093 A1     Oct. 8, 2020

Related U.S. Application Data (60) Provisional application No. 62/828,750, filed on Apr. 3, 2019.

(51) Int. Cl.
     *G01N 21/31*      (2006.01)
     *G01N 21/39*      (2006.01)
     (Continued)

(52) U.S. Cl.
CPC ............ *G01N 21/39* (2013.01); *G01J 3/0205* (2013.01); *G01J 3/10* (2013.01); *G01J 3/42* (2013.01);
(Continued)

(58) Field of Classification Search
CPC ............ G01N 21/31; G01N 2021/391; G01N 21/3504; G01N 21/39; G01N 21/274; G01N 21/27; G01N 21/031; G01N 2021/0346; G01N 21/783; G01N 2021/1704; G01J 3/42; G01J 3/0205; G01J 2003/423;
(Continued)

(56) References Cited

U.S. PATENT DOCUMENTS

| | | | |
|---|---|---|---|
| 3,431,514 A | 3/1969 | Oshman et al. | |
| 3,453,557 A | 7/1969 | Polanyi et al. | |

(Continued)

FOREIGN PATENT DOCUMENTS

| | | |
|---|---|---|
| CA | 2792032 A1 | 9/2011 |
| CA | 2997070 A1 | 9/2019 |

(Continued)

OTHER PUBLICATIONS

Orr et al. "Cavity ringdown spectroscopy with widely tunable swept-frequency lasers," European Quantum Eletronics Conference, 2005 *EQEC '05) Jun. 12-17, 2005, p. 204.

(Continued)

*Primary Examiner* — Mohamed K Amara
(74) *Attorney, Agent, or Firm* — Millman IP Inc.

(57) ABSTRACT

A cavity ring-down spectroscopy system and a method of modulating a light beam therein are provided. The cavity ring-down spectroscopy system includes at least one laser that generates a light beam, a first optical modulator positioned to attenuate the light beam from the at least one laser, a second optical modulator positioned to attenuate the light beam from the first optical modulator, a ring-down cavity positioned to receive the light beam from the second optical modulator, and at least one light sensor to detect an intensity of light leaked from the ring-down cavity.

6 Claims, 2 Drawing Sheets

(51) Int. Cl.
  *G01N 33/497* (2006.01)
  *G01N 1/40* (2006.01)
  *G01J 3/42* (2006.01)
  *G01N 21/3504* (2014.01)
  *G01N 21/552* (2014.01)
  *G01J 3/02* (2006.01)
  *G01J 3/10* (2006.01)
  *G06N 20/00* (2019.01)
  *G01N 21/77* (2006.01)

(52) U.S. Cl.
  CPC .............. *G01N 1/40* (2013.01); *G01N 21/31* (2013.01); *G01N 21/3504* (2013.01); *G01N 21/552* (2013.01); *G01N 33/497* (2013.01); *G01J 2003/423* (2013.01); *G01N 2021/391* (2013.01); *G01N 2021/398* (2013.01); *G01N 2021/7789* (2013.01); *G01N 2033/4975* (2013.01); *G06N 20/00* (2019.01)

(58) Field of Classification Search
  CPC .... G01J 3/02; G01J 3/10; G01J 3/0208; G01J 3/0229; G01J 3/1256; G01J 2003/262; G01J 3/0237; G01J 3/08; H01S 5/141; H01S 3/1068; H01S 3/11; H01S 3/113; H01S 3/117; H01S 3/1106; H01S 3/107; H01S 3/108; H01S 3/0085; H01S 3/083; H01S 3/115; G02F 1/11
  See application file for complete search history.

(56) References Cited

U.S. PATENT DOCUMENTS

| | | | |
|---|---|---|---|
| 3,517,330 A | 6/1970 | Doyle et al. | |
| 3,534,289 A | 10/1970 | Clark et al. | |
| 3,596,201 A | 7/1971 | Chester | |
| 3,628,173 A | 12/1971 | Danielmeyer | |
| 3,733,129 A | 5/1973 | Bridges | |
| 4,197,513 A | 4/1980 | Bell et al. | |
| 4,410,271 A | 10/1983 | Matthews | |
| 4,468,773 A | 8/1984 | Seaton | |
| 4,475,199 A | 10/1984 | Sanders et al. | |
| 4,648,714 A | 3/1987 | Benner et al. | |
| 4,672,618 A | 6/1987 | Wijntjes et al. | |
| 4,779,279 A | 10/1988 | Brown | |
| 4,784,486 A | 11/1988 | Van Wagenen et al. | |
| 4,964,132 A | 10/1990 | Fischer | |
| 5,014,278 A | 5/1991 | Deki | |
| 5,029,174 A | 7/1991 | Anderson | |
| 5,054,027 A | 10/1991 | Goodberlet et al. | |
| 5,091,912 A | 2/1992 | Bretenaker et al. | |
| 5,135,304 A | 8/1992 | Miles et al. | |
| 5,465,728 A | 11/1995 | Phillips | |
| 5,528,040 A | 6/1996 | Lehmann | |
| 5,573,005 A | 11/1996 | Ueda et al. | |
| 5,646,952 A | 7/1997 | Whittley | |
| 5,815,277 A | 9/1998 | Zare et al. | |
| 5,903,358 A | 5/1999 | Zare et al. | |
| 5,912,740 A | 6/1999 | Zare et al. | |
| 6,076,392 A | 6/2000 | Drzewiecki | |
| 6,084,682 A | 7/2000 | Zare et al. | |
| 6,233,052 B1 | 5/2001 | Zare et al. | |
| 6,324,191 B1 | 11/2001 | Horvath | |
| 6,363,772 B1 | 4/2002 | Berry | |
| 6,466,322 B1 | 10/2002 | Paldus et al. | |
| 6,479,019 B1 | 11/2002 | Goldstein et al. | |
| 6,504,145 B1 | 1/2003 | Romanini et al. | |
| 6,540,691 B1 | 4/2003 | Phillips | |
| 6,563,583 B2 | 5/2003 | Ortyn et al. | |
| 6,582,376 B2 | 6/2003 | Baghdassarian | |
| 6,633,596 B1 | 10/2003 | Wulfmeyer et al. | |
| 6,658,034 B2 * | 12/2003 | Gamache ............... H01S 5/141 | |
| | | | 372/45.01 |
| 6,726,637 B2 | 4/2004 | Phillips | |
| 6,727,492 B1 | 4/2004 | Ye et al. | |
| 6,865,198 B2 | 3/2005 | Taubman | |
| 6,952,945 B2 | 10/2005 | O'Brien | |
| 7,004,909 B1 | 2/2006 | Patel et al. | |
| 7,012,696 B2 | 3/2006 | Orr et al. | |
| 7,069,769 B2 * | 7/2006 | Kung ................. G01N 33/0039 | |
| | | | 73/24.02 |
| 7,101,340 B1 * | 9/2006 | Braun .................... A61B 5/097 | |
| | | | 128/920 |
| 7,106,763 B2 | 9/2006 | Tan et al. | |
| 7,235,054 B2 | 6/2007 | Eckerbom | |
| 7,352,463 B2 | 4/2008 | Bounaix | |
| 7,391,517 B2 | 6/2008 | Trebbia et al. | |
| 7,450,240 B2 | 11/2008 | Morville et al. | |
| 7,535,573 B2 * | 5/2009 | Kachanov ................. G01J 3/42 | |
| | | | 356/437 |
| 7,538,881 B2 * | 5/2009 | Ye ............................ G01J 3/26 | |
| | | | 356/454 |
| 7,541,586 B2 | 6/2009 | Miller | |
| 7,555,024 B2 | 6/2009 | Ishaaya et al. | |
| 7,569,823 B2 | 8/2009 | Miller | |
| 7,606,274 B2 | 10/2009 | Mirov et al. | |
| 7,612,885 B2 | 11/2009 | Cole et al. | |
| 7,613,216 B2 | 11/2009 | Nakagawa | |
| 7,616,123 B2 | 11/2009 | Ridder et al. | |
| 7,646,485 B2 | 1/2010 | Tan | |
| 7,679,750 B2 | 3/2010 | Li et al. | |
| 7,902,534 B2 | 3/2011 | Cole et al. | |
| 8,018,981 B2 | 9/2011 | Eckles et al. | |
| 8,109,128 B2 * | 2/2012 | Kalkman ............ G01N 29/2425 | |
| | | | 73/24.02 |
| 8,288,727 B2 | 10/2012 | Cormier et al. | |
| 8,322,190 B2 * | 12/2012 | Kalkman ................ A61B 5/083 | |
| | | | 73/24.02 |
| 8,437,000 B2 * | 5/2013 | Cole ..................... G01N 21/3151 | |
| | | | 356/437 |
| 8,488,639 B1 | 7/2013 | Diels et al. | |
| 8,564,785 B2 * | 10/2013 | Newbury .................. G01J 3/453 | |
| | | | 356/451 |
| 8,642,982 B2 * | 2/2014 | Plusquellic ............... G01J 3/108 | |
| | | | 250/493.1 |
| 8,659,758 B2 | 2/2014 | Koulikov et al. | |
| 8,659,759 B2 | 2/2014 | Koulikov et al. | |
| 8,665,442 B2 | 3/2014 | Koulikov et al. | |
| 8,885,167 B2 | 11/2014 | Koulikov et al. | |
| 8,958,446 B2 | 2/2015 | Hirose | |
| 8,982,352 B1 | 3/2015 | Hoffnagle et al. | |
| 9,014,221 B2 | 4/2015 | Kub et al. | |
| 9,029,819 B2 * | 5/2015 | Zhu ........................ G01N 21/39 | |
| | | | 250/565 |
| 9,097,583 B2 | 8/2015 | Gupta et al. | |
| 9,194,742 B2 | 11/2015 | Kachanov et al. | |
| 9,207,121 B2 * | 12/2015 | Adler ....................... G01J 3/021 | |
| 9,212,990 B1 | 12/2015 | Muraviev | |
| 9,568,465 B2 | 2/2017 | Rihani et al. | |
| 9,625,702 B2 | 4/2017 | Hodges et al. | |
| 9,653,877 B1 * | 5/2017 | Arissian ................. H01S 3/1112 | |
| 9,671,332 B2 | 6/2017 | Christensen | |
| 9,755,399 B2 * | 9/2017 | Tulip ...................... G01N 21/39 | |
| 9,768,347 B2 | 9/2017 | Teo et al. | |
| 9,778,110 B1 | 10/2017 | Rella et al. | |
| 9,918,661 B2 * | 3/2018 | Cormier ................. A61B 5/0836 | |
| 10,034,621 B2 | 7/2018 | Wondka et al. | |
| 10,101,268 B2 * | 10/2018 | Apolonskiy ......... C07D 231/12 | |
| 10,130,284 B2 | 11/2018 | Johnson | |
| 10,139,392 B2 | 11/2018 | Kaariainen et al. | |
| 10,141,713 B2 * | 11/2018 | Kim ....................... H01S 3/1312 | |
| 10,168,275 B2 | 1/2019 | Orcutt | |
| 10,194,833 B2 | 2/2019 | Cormier | |
| 10,234,381 B2 | 3/2019 | Koulikov | |
| 10,330,592 B2 | 6/2019 | Koulikov | |
| 10,401,281 B2 | 9/2019 | Koulikov | |
| 10,499,819 B2 | 12/2019 | Wondka et al. | |
| 10,514,299 B2 * | 12/2019 | Koulikov ............ G01N 21/3504 | |
| 10,527,492 B2 | 1/2020 | Bouzid | |
| 10,620,048 B2 * | 4/2020 | Allison .................... G01J 3/02 | |
| 2001/0003482 A1 * | 6/2001 | Zare ....................... G01N 21/39 | |
| | | | 356/432 |

(56) References Cited

U.S. PATENT DOCUMENTS

| | | |
|---|---|---|
| 2003/0109794 A1 | 6/2003 | Phillips |
| 2003/0189711 A1* | 10/2003 | Orr .................. G01N 21/39 356/484 |
| 2004/0022281 A1 | 2/2004 | Steffens et al. |
| 2004/0065816 A1* | 4/2004 | Ye .................. G01J 3/42 250/227.18 |
| 2004/0137637 A1* | 7/2004 | Wang .................. G01N 21/33 436/128 |
| 2004/0142484 A1 | 7/2004 | Berlin et al. |
| 2004/0162500 A1 | 8/2004 | Kline |
| 2004/0190563 A1 | 9/2004 | Gendron |
| 2005/0134836 A1 | 6/2005 | Paldus et al. |
| 2005/0177056 A1 | 8/2005 | Giron et al. |
| 2005/0177057 A1 | 8/2005 | Friedman et al. |
| 2005/0201428 A1 | 9/2005 | Cotteverte et al. |
| 2005/0213617 A1 | 9/2005 | Gendron |
| 2005/0254535 A1* | 11/2005 | Loewen .................. G21K 1/06 372/32 |
| 2006/0200037 A1 | 9/2006 | Falasco |
| 2006/0233205 A1 | 10/2006 | Farmiga et al. |
| 2007/0008995 A1 | 1/2007 | Oozeki et al. |
| 2007/0062255 A1 | 3/2007 | Talton |
| 2007/0091941 A1 | 4/2007 | Mori et al. |
| 2007/0133001 A1 | 6/2007 | Cox et al. |
| 2007/0268941 A1* | 11/2007 | Kim .................. H01S 5/141 372/22 |
| 2008/0091085 A1 | 4/2008 | Urushihata et al. |
| 2008/0139021 A1 | 6/2008 | Suzuki et al. |
| 2008/0170597 A1 | 7/2008 | van der Veer |
| 2009/0201957 A1 | 8/2009 | Brotherton-Ratcliffe |
| 2009/0232172 A1 | 9/2009 | Masuda et al. |
| 2009/0306527 A1 | 12/2009 | Kubo et al. |
| 2010/0002234 A1 | 1/2010 | Cormier et al. |
| 2010/0074089 A1 | 3/2010 | Smith et al. |
| 2010/0135342 A1 | 6/2010 | Livas et al. |
| 2011/0072887 A1 | 3/2011 | Oki |
| 2011/0214479 A1* | 9/2011 | Kachanov .......... G01N 21/1702 73/24.02 |
| 2011/0216311 A1 | 9/2011 | Kachanov et al. |
| 2011/0269632 A1 | 11/2011 | Haick |
| 2011/0295140 A1 | 12/2011 | Zaidi et al. |
| 2012/0143805 A1 | 6/2012 | Gold et al. |
| 2012/0250706 A1 | 10/2012 | Stiens et al. |
| 2012/0266883 A1 | 10/2012 | Taylor et al. |
| 2012/0309048 A1 | 12/2012 | Ratcliffe et al. |
| 2013/0144561 A1 | 6/2013 | Harb et al. |
| 2013/0228688 A1* | 9/2013 | Plusquellic .............. G01J 3/26 250/339.06 |
| 2013/0303929 A1 | 11/2013 | Martino et al. |
| 2014/0123729 A1* | 5/2014 | Kachanov .............. G01N 21/39 73/24.02 |
| 2014/0125993 A1* | 5/2014 | Kachanov .............. G01N 21/39 356/519 |
| 2014/0293283 A1 | 10/2014 | Farooq et al. |
| 2014/0320856 A1 | 10/2014 | McKeever et al. |
| 2015/0032019 A1 | 1/2015 | Acker et al. |
| 2015/0077747 A1 | 3/2015 | Smith et al. |
| 2015/0138558 A1* | 5/2015 | Kachanov .......... G01N 33/0062 356/437 |
| 2015/0335267 A1 | 11/2015 | Cormier et al. |
| 2016/0069795 A1* | 3/2016 | Koulikov .............. G02B 7/181 356/437 |
| 2016/0174875 A1 | 6/2016 | Forster et al. |
| 2016/0285236 A1 | 9/2016 | Yvind |
| 2016/0313233 A1* | 10/2016 | Zangmeister ...... G01N 21/1702 |
| 2017/0074857 A1 | 3/2017 | Dennis et al. |
| 2017/0373462 A1 | 12/2017 | Guzman et al. |
| 2018/0059003 A1 | 3/2018 | Jourdainne |
| 2018/0156718 A1 | 6/2018 | Fleisher et al. |
| 2018/0202918 A1 | 7/2018 | Tanaka et al. |
| 2018/0202923 A1 | 7/2018 | Kageyama et al. |
| 2018/0212396 A1 | 7/2018 | Kim et al. |
| 2018/0214050 A1 | 8/2018 | Purves |
| 2018/0261974 A1 | 9/2018 | Purves et al. |
| 2018/0350304 A1 | 12/2018 | Ishii |
| 2019/0265159 A1 | 8/2019 | Koulikov |
| 2019/0265160 A1 | 8/2019 | Koulikov |
| 2019/0271641 A1 | 9/2019 | Koulikov |
| 2019/0301933 A1 | 10/2019 | Allison |
| 2019/0323955 A1 | 10/2019 | Koulikov |

FOREIGN PATENT DOCUMENTS

| | | |
|---|---|---|
| CN | 101470072 A | 7/2009 |
| CN | 102316801 B | 1/2012 |
| CN | 102798631 A | 11/2012 |
| CN | 102841082 A | 12/2012 |
| CN | 102264292 B | 5/2014 |
| CN | 106908389 A | 6/2017 |
| CN | 107037003 A | 8/2017 |
| CN | 106981552 B | 4/2019 |
| CN | 109856054 A | 6/2019 |
| DE | 2130331 A1 | 3/1977 |
| DE | 2723939 A1 | 12/1978 |
| DE | 3819687 A1 | 12/1989 |
| DE | 10156149 A1 | 6/2003 |
| EP | 557658 A1 | 9/1993 |
| EP | 600711 A2 | 6/1994 |
| EP | 1535047 B1 | 6/2005 |
| EP | 1304955 B1 | 12/2008 |
| EP | 1997198 B1 | 6/2012 |
| EP | 1418842 B1 | 7/2012 |
| EP | 3037805 A1 | 6/2016 |
| EP | 2745097 B1 | 2/2018 |
| EP | 3419122 A1 | 12/2018 |
| EP | 3467473 A1 | 4/2019 |
| GB | 1019295 A | 2/1966 |
| JP | 2001194299 A | 7/2001 |
| JP | 2006189392 A | 7/2006 |
| JP | 2006226727 A | 8/2006 |
| JP | 2010243270 A | 10/2010 |
| JP | 2013011620 A | 1/2013 |
| JP | 5341519 B2 | 11/2013 |
| JP | 5537174 B2 | 7/2014 |
| JP | 2016503904 A | 2/2016 |
| WO | 2090935 | 11/2002 |
| WO | 2005038436 A2 | 4/2005 |
| WO | 2005076875 A2 | 8/2005 |
| WO | 2005088274 A1 | 9/2005 |
| WO | 2017142644 A1 | 12/2007 |
| WO | 2011117572 A1 | 9/2011 |
| WO | 2012004794 A1 | 1/2012 |
| WO | 2014070952 A1 | 5/2014 |
| WO | 2018142027 A1 | 8/2018 |
| WO | 2019239827 A1 | 12/2019 |

OTHER PUBLICATIONS

ISR for PCT/CA2007/002306 mailed Apr. 17, 2008.
Office action for CA2671122 dated Jun. 13, 2011.
Harren et al., Photoacoustic Spectroscopy in Trace Gas Monitoring, encyclopedia of Analytical Chemistry, pp. 2203-2226, J. Wiley and Sons, 2000.
Freed, C., Status of $CO_2$ Isotope Lasers and Their Applications in Turnable Laser Spectroscopy, IEEE Journal of Quantum Electronics, vol. QE-18, No. 8, 1982.
Sharpe et al., "Gas Phase Databases for Quantitative Infrared Spectroscopy," Applied Spectroscopy, vol. 58, No. 12, 2004.
Akaike, H., "A new look at the statistical model identification," IEEE Transactions on Automatic Control, 19(6): 716-723, 1974.
Cormier, John G., "Development of an Infrared Cavity Ringdown Spectroscopy Experiment and Measurements of Water Vapor Continuum Absorption.," Thesis, 2002.
Kurochkin et al., "Three Mirror Cavity $CO_2$ Lser for Inactivity Saturated-Absorption Spectroscopy." Optical Spectroscopy, vol. 65, No. 2, pp. 265-267, Aug. 1988.
Office Action for U.S. Appl. No. 12/517,036 dated Dec. 14, 2011.
Fuchs, D., et al., "Decline of exhaled isoprene in lung cancer patients correlates with immune activation," Journal of breath research 6.2 (2012): 027101+B8.

(56) References Cited

OTHER PUBLICATIONS

Ligor, Magdalena, et al., "Determination of volatile organic compounds of exhaled breath of patients with lung cancer using solid phase microextraction and gas chromatography mass spectrometry," Clinical chemistry and laboratory medicine 47.5 (2009): 550-560.
Vaughan, Christina, et al., "Automated determination of seven phenolic compounds in mainstream tobacco smoke," Nicotine and Tobacco Research 10.7 (2008): 1261-1268.
Cope, et al., "Effects of ventilation on the collection of exhaled breath in humans," J. App I Physiol 96: 1371-1379: 2004.
Office action for U.S. Appl. No. 14/720,447 dated Apr. 6, 2017.
Office action for U.S. Appl. No. 14/720,447 dated Apr. 19, 2018.
Final office action for U.S. Appl. No. 14/720,447 dated Sep. 13, 2017.
English translation of DE102013215640A1.
Office action for U.S. Appl. No. 14/720,456 dated Jun. 14, 2017.
Office action for U.S. Appl. No. 15/920,212 dated Jun. 27, 2019.
Final Office action for U.S. Appl. No. 15/920,212 dated Oct. 3, 2019.
Notice of Allowance for U.S. Appl. No. 15/920,212 dated Jan. 23, 2020.
International Search Report and Written Opinion for PCT/CA2020/050252 dated May 12, 2020.
International Search Report and Written Opinion for PCT/CA2020/050250 dated May 22, 2020.
International Search Report and Written Opinion for PCT/CA2020/050/249 dated Apr. 29, 2020.
International Search Report and Written Opinion for PCT/CA2020/050248 datd Jun. 11, 2020.
Office action for U.S. Appl. No. 15/917,225 dated Mar. 9, 2020.
Office action for U.S. Appl. No. 15/917,225 dated May 14, 2020.
Office Action for U.S. Appl. No. 16/564,662 dated Aug. 10, 2020.

\* cited by examiner

CAVITY RING-DOWN SPECTROSCOPY SYSTEM AND METHOD OF MODULATING A LIGHT BEAM THEREIN

CROSS-REFERENCE TO RELATED APPLICATIONS

This application claims the benefit of U.S. Provisional Application No. 62/828,750, filed Apr. 3, 2019, the contents of which are incorporated herein by reference in their entirety.

FIELD

The specification relates generally to gaseous sample analysis, and, in particular, to a cavity ring-down spectroscopy system and a method of modulating a light beam therein.

BACKGROUND OF THE DISCLOSURE

Cavity ring-down spectroscopy ("CRDS") is an approach that is generally used to identify and quantify a single analyte in a gaseous sample using their absorption spectra. A typical CRDS system employs a laser generating a beam that is directed into a cavity of a chamber having two highly reflective mirrors. The beam is normally within the visible light spectrum, often in the near infrared ("IR") spectrum, and is tuned to a single wavelength to identify the presence of a single molecule. The beam is then reflected repeatedly between the mirrors, which allow a fraction of the light to escape the ring-down cavity. When the laser is in resonance with a cavity mode, intensity builds up in the cavity due to constructive interference. When the light entering the cavity is extinguished, the intensity of the light in the ring-down cavity, when empty, decays at a pre-determined rate. A small fraction of the light is not reflected by the mirrors and escapes the ring-down cavity. The intensity of the escaping light is measured by a sensor component to determine the decay rate.

When the gaseous sample is placed in the ring-down cavity, analytes present in the gaseous sample absorb some of the light, thereby accelerating the decay of the intensity of the light in the ring-down cavity. Absorption spectra are generated by measuring the decay times of the light in the presence of the gaseous sample at specific wavelengths relative to the decay times of the light in the absence of the gaseous sample at these wavelengths. A linear regression of the measured absorption spectra for the gaseous sample with the known absorption spectra of various analytes enables the identification and quantification of individual analytes in the gaseous sample.

SUMMARY OF THE DISCLOSURE

In one aspect, there is provided a cavity ring-down spectroscopy system, comprising at least one laser that generates a light beam, a first optical modulator positioned to attenuate the light beam from the at least one laser, a second optical modulator positioned to attenuate the light beam from the first optical modulator, a ring-down cavity positioned to receive the light beam from the second optical modulator, and at least one light sensor to measure an intensity of light leaked from the ring-down cavity.

The cavity ring-down spectroscopy system can further include at least one focusing lens for focusing the light beam to match an optical mode of the ring-down cavity.

The first and second optical modulators can be acousto-optic modulators.

The cavity ring-down spectroscopy system can further comprise a controller that is configured to direct the first optical modulator to attenuate the light beam at or close to an attenuation limit of the first optical modulator and to simultaneously direct the second optical modulator to further attenuate the light beam at or close to an attenuation limit of the second optical modulator to reduce or extinguish an intensity of the light beam from the first optical modulator.

In another aspect, there is provided a method of modulating a light beam in a cavity ring-down spectroscopy system, comprising: generating a light beam via at least one laser; extinguishing the light beam from the at least one laser via a first optical modulator; extinguishing the light beam from the first optical modulator via a second optical modulator; receiving the light beam attenuated by the second optical modulator in a ring-down cavity; and measuring a rate of decay of light leaked from the ring-down cavity.

The first and second optical modulators can be acousto-optic modulators.

The method can further comprise: directing the first optical modulator to attenuate the light beam at or close to an attenuation limit of the first optical modulator; and simultaneously directing the second optical modulator to further attenuate the light beam travelling towards the ring-down cavity at or close to an attenuation limit of the second optical modulator to reduce or extinguish an intensity of the light beam from the first optical modulator.

Other technical advantages may become readily apparent to one of ordinary skill in the art after review of the following figures and description.

BRIEF DESCRIPTIONS OF THE DRAWINGS

For a better understanding of the embodiment(s) described herein and to show more clearly how the embodiment(s) may be carried into effect, reference will now be made, by way of example only, to the accompanying drawings in which.

Unless otherwise specifically noted, articles depicted in the drawings are not necessarily drawn to scale.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiment or embodiments described herein. However, it will be understood by those of ordinary skill in the art that the embodiments described herein may be practiced without these specific details. In other instances, well-known methods, procedures and components have not been described in detail so as not to obscure the embodiments described herein. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

CRDS systems typically include an optical modulator to modulate light from a laser. The optical modulator may deflect the light to another path in order to attenuate the intensity or power of the light. Acousto-optic modulators ("AOMs") are one type of optical modulator that uses a piezoelectric transducer coupled to a material such as germanium or glass. In the described embodiment, the material is germanium. When an oscillating electric signal is applied to the piezoelectric transducer, the piezoelectric transducer vibrates, creating sound waves in the material. These sound waves expand and compress the material, thereby creating periodic variations in the refractive index and allowing for Bragg diffraction. Light entering the AOM at the first order Bragg angle relative to the plane perpendicular to the axis or propagation of the acoustic wave will be deflected by an amount equal to twice the Bragg angle at maximum efficiency. Extinguishing the electric signal removes the Bragg diffraction properties of the material and causes the light to pass through undeflected, effectively attenuating the light along the deflected optical path. A by-product of the AOM is that the frequency of the light being deflected is shifted.

An electro-optic modulator is another type of optical modulator that applies a DC or low-frequency electric field to a material to distort the position, orientation, and/or shape of the molecules of the material. As a result, the refractive index is altered to change the phase of the outgoing beam as a function of the applied field. By sending the beam through a polarizer, the phase modulation is converted to intensity modulation. In another method, a phase modulator when placed in a branch of an interferometer can act as an intensity modulator.

The optical modulators are used to control the intensity of the light beam generated by the laser. One side effect of the use of acousto-optic modulators is that the frequency of the light is shifted. This shift is small relative to the absolute frequency of the light.

In CRDS, the rate of decay of light in the ring-down cavity is determined in order to understand the absorption spectrum(s) of the gaseous sample in the ring-down cavity. Traditional CRDS systems employing a single optical modulator, however, have difficulties extinguishing light supplied to the ring-down cavity as quickly and completely as desirable. This can be more true for mid-IR than for near-IR and visible wavelengths. Generally, an optical modulator does not operate to generate perfect step function output, and has ramp up and ramp down times. As a result, the additional light entering the ring-down cavity at the start of a ring-down event can be difficult to compensate for, making linear regression with known analyte absorption spectra more challenging.

Figure 1:
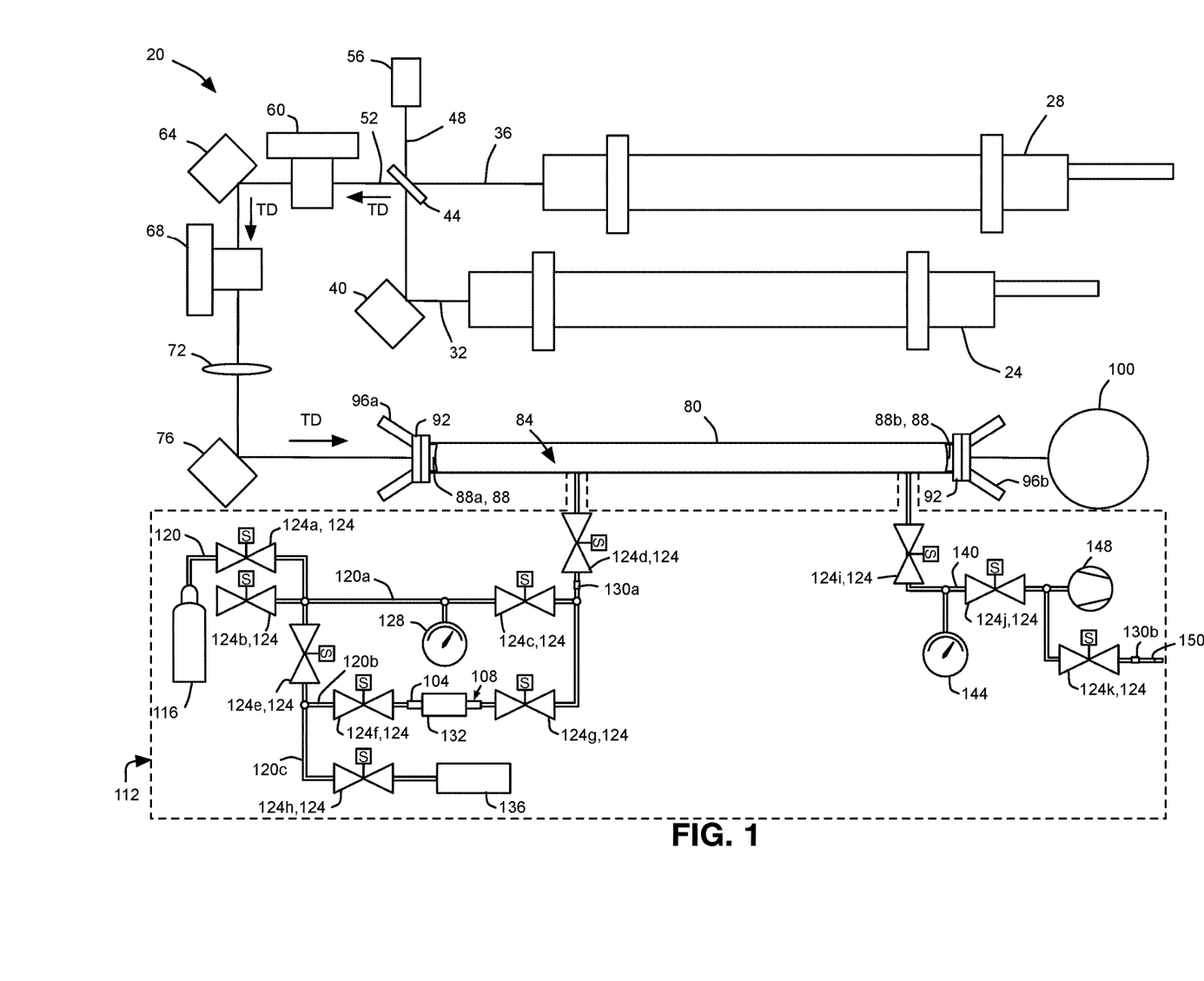
FIG. 1 is a schematic diagram of various optical and pneumatic components of a cavity ring-down spectroscopy system in accordance with one embodiment.

Various components of a CRDS system 20 in accordance with a particular embodiment are shown in FIG. 1. A $CO_2$ laser 24 and a carbon-13 $O_2$ laser 28 are provided. The $CO_2$ laser 24 and the carbon-13 $O_2$ laser 28 are gas tube lasers that emit at a series of quasi-evenly-spaced, well-known frequencies that can be rapidly selected using an adjustable diffraction grating apparatus. Gas tube laser technology has a long history and is a stable and robust way of generating infrared radiation at precisely-known frequencies. Both the $CO_2$ laser 24 and the carbon-13 $O_2$ laser 28 emit light in the mid-IR spectrum.

Each of the $CO_2$ laser 24 and the carbon-13 $O_2$ laser 28 has an actuator and an output coupler that enable adjustment of the length of the laser cavity as well as change the angle of grating at the back of the cavity, thereby changing its pitch to adjust which wavelengths it reflects. By both adjusting the length of the laser cavity and changing the angle of the grating, the laser can be very accurately tuned to a specific wavelength and desired mode quality.

The $CO_2$ laser 24 produces a first laser beam 32, and the carbon-13 $O_2$ laser 28 produces a second laser beam 36. Depending on the light frequency desired, either the $CO_2$ laser 24 is tuned and generates the first laser beam 32 while the carbon-13 $O_2$ laser 28 is detuned, or the carbon-13 $O_2$ laser 28 is tuned and generates the second laser beam 36 while the $CO_2$ laser 24 is detuned. In this manner, at most only one of the $CO_2$ laser 24 and the carbon-13 $O_2$ laser 28 outputs a beam at any particular time so that the first beam 32 and the second beam 36 are not combined simultaneously. Mid-infrared, and specifically long wavelength infrared, was chosen as the type of light as most volatile organic compounds absorb light in this range. As a result, multiple volatile organic compounds can be measured by a single system. CO2 lasers operate in this range and have sufficient power and linewidth narrowness for ring-down spectroscopy. Using two lasers adds to the range and number of available wavelengths that the CRDS system 20 can use to analyze gaseous samples.

The first laser beam 32 is redirected via a mirror 40 on an optic mount towards a beam splitter 44. The beam splitter 44 is partially reflective and partially transmissive, and splits each of the first laser beam 32 and the second laser beam 36 into two beams, a sampling beam 48, and a working beam 52 that has the same characteristics as the sampling beam 48 and can be of similar intensity as the sampling beam 48.

The sampling beam 48 is received by a fast detector 56. The fast detector 56 measures the amplitude and the beat frequency of the sampling beam 48 using an oscilloscope. The beat frequency can indicate the presence of higher order modes resulting from a less-than-optimal tuning of the $CO_2$ laser 24 or the carbon-13 $O_2$ laser 28. In response to the detection of an undesirable beat frequency, the corresponding laser 24 or 28 is tuned until the amplitude of the beat frequency is minimized or eliminated while maximizing the intensity. If the amplitude of the beat frequency cannot be reduced below an acceptable level, the laser can be tuned to a different wavelength.

The working beam 52 continues to a first optical modulator 60, which then deflects the working beam 52 to a mirror 64 on an optic mount. The mirror 64 redirects the light towards a second optical modulator 68 that, in turn, deflects the working beam 52 to a focusing lens 72. In the present embodiment, the first and second optical modulators 60, 68 are AOMs, also referred to as Bragg cells, but could also be electro-optic modulators in other embodiments.

The first and second optical modulators 60, 68 act as attenuators to adjust the intensity of the working beam 52 and extinguish the beam at the commencement of a ring-down event. As they are AOMs, the first and second optical modulators 60, 68 use the acousto-optic effect to diffract the light using sound waves (normally at radio-frequency). In each of the first and second optical modulators, a piezoelectric transducer is coupled to a material such as germanium or glass, and an oscillating electric signal is used to cause the piezoelectric transducer to vibrate. The vibrating piezoelectric transducer creates sound waves in the material that expand and compress the material, thereby creating period variations in the refractive index and allowing for Bragg diffraction. Light entering the AOM at Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively extinguishing the light along the deflected optical path. Hence, the intensity of the sound can be used to modulate the intensity of the light in the deflected beam.

The intensity of the light deflected by each of the first and second optical modulators 60, 68 can be between about 85%, representing a maximum deflection efficiency of the optical modulators 60, 68, and an attenuation limit of each of the first and second optical modulators 60, 68 of about 0.1% of the input light intensity. When the acoustic wave applied to the germanium is turned off, the deflected beam loses about 30 dB, or 99.9%, of the previous intensity. The attenuation limit means the upper limit of how much of the input light intensity can be reduced by the optical modulator.

Optic modulators are asymmetrical in that, as a side effect, they Doppler-shift the frequency of light in a first mode when the input light is received at a first end thereof, and they Doppler-shift the frequency of light in a second mode that is counter to the first mode when the input light is received at a second end thereof and the attenuation power is the same. The Doppler shift of the frequency of the light is, however, in the same direction regardless of whether the light enters at a first end or at a second end.

Conventional CRDS systems use a single optical modulator and, as a result, have a working beam that is frequency shifted. These frequency shifts are generally small in relation to the frequency of the light, and can change the manner in which the light is absorbed by matter in the cavity, but this frequency shift can be compensated for during the analysis. If diffraction is towards the acoustic wave source of an AOM, the frequency shift is downwards, and if diffraction is away from the acoustic wave source, the frequency shift is upwards. As discussed, the effect is minimal.

The working beam 52 deflected by the second optical modulator 68 is focused via a focusing lens 72 to match an optical mode of the ring-down cavity 84. As the laser beam, and thus the working beam 52, travels from the $CO_2$ laser 24 or the carbon-13 $O_2$ laser 28, it continues to diverge. The focusing lens 72 focuses the working beam 52 back down.

A mirror 76 on an optic mount thereafter redirects the working beam 52 towards a ring-down chamber 80. The two mirrors 64, 76 extend the length of the path of the working beam 52.

The ring-down chamber 80 is an elongated tube defining a ring-down cavity 84 therein. A front cavity mirror 88a and a rear cavity mirror 88b (alternatively referred to herein as cavity mirrors 88) are positioned at longitudinal ends of the ring-down cavity 84. The cavity mirrors 88 are highly reflective, both to light directed to the cavity mirrors 88 from outside of the ring-down cavity 84 and directed to the cavity mirrors 88 within the ring-down cavity 84. As a result, a fraction of the working beam 52 is directed at the front cavity mirror 88a, about 0.1%, passes through the front cavity mirror 88a, and enters the ring-down cavity 84, and the majority of the working beam 52, about 99.9% is reflected back towards the mirror 76.

The cavity mirrors 88 are mounted on mirror mounts 92 that are actuatable to adjust the positioning and orientation of the cavity mirrors 88. In particular, the front cavity mirror 88a towards the front of the ring-down cavity 84 is mounted on a mirror mount 92 that is actuatable via three mechanized micrometers 96a. The rear cavity mirror 88b towards the rear of the ring-down cavity 84 is mounted on a mirror mount 92 that is actuatable via three motorized micrometers 96b that can be manually adjusted for optical alignment or with a piezo that allows them to be adjusted further with the piezo driver.

The angle of each of cavity mirror 88 can be changed so that they are perfectly aligned so that when a light beam enters the ring-down cavity 84, the light beam does not deviate. If one of the cavity mirrors 88 is askew, then some of the light gets reflected to the side of the ring-down cavity 84, intensity of the light is lost, high-order modes result, amongst other things. The micrometers 96 can also be simultaneously tuned to change the length of the ring-down cavity 84. This allows for the tuning of the ring-down cavity 84 so that the ring-down cavity 84 resonates at the frequency of the light that is entering the ring-down cavity 84.

The focusing lens 72 focuses the laser light to match the optical mode of the ring-down cavity 84, so that the minimum waist of the beam is positioned at the same place as the minimum beam waist of the ring-down cavity 84.

A light sensor in the form of a liquid nitrogen-cooled detector 100 is positioned behind the rear cavity mirror 88b to receive light escaping through it. The liquid nitrogen-cooled detector 100 measures the intensity of the light that escapes the ring-down cavity 84. Other types of sensors for measuring the intensity of the escaping light can be used in place of the liquid nitrogen-cooled detector 100, such as a thermo-electrically cooled detector.

During a tuning process, one of the $CO_2$ laser 24 and the carbon-13 $O_2$ laser 28 is tuned and the sampling beam 48 reaching the fast detector 56 is analyzed to identify a beat frequency. If a beat frequency is present in the sampling beam 48, the corresponding laser is adjusted until the undesirable beat frequency is removed or diminished in amplitude below an acceptable limit.

In addition, the position of the cavity mirrors 88 are adjusted via the micrometers 96 so that no higher order modes are present in the ring-down cavity 84.

Gaseous samples are loaded into the ring-down cavity 84 from a thermal desorption tube 104 that is used to collect the gaseous samples for testing. Thermal desorption tubes are generally made of stainless steel and contain various types of solid adsorbent material. The solid sorbents are selected for sampling specific compounds to trap and retain the compounds of interest even in the presence of other compounds, and allow the collected compounds to be easily desorbed or extracted for analysis. In addition, the solid sorbents which are selected do not react with the compounds of interest.

In a particular example, the gaseous samples are human breath samples collected from patients. A receiving end 108 of the thermal desorption tube 104 receives human breath collected from a human for testing. As a result, compounds of interest are more concentrated towards the receiving end 108 of the thermal desorption tube 104.

A pneumatic system 112 is used to load gaseous samples from thermal desorption tubes 104 into the ring-down cavity 84, and evacuate the pneumatic system 112, including the ring-down cavity 84. During loading of a gaseous sample, the pneumatic system 112 fills the ring-down cavity 84 with the gaseous sample that has been collected (i.e., to desorb the gaseous sample from the thermal desorption tube 104, get the gaseous sample into the ring-down cavity 84 without introducing contaminants), brings the pressure and temperature in the ring-down cavity to one atmosphere and 50 degrees Celsius, and seals the ring-down cavity 84. In this embodiment, the absorption spectra for a set of samples to which the measured absorption spectra are compared are determined at this pressure and temperature to ensure consistency between these parameters which can affect the results. In other embodiments, however, the pressure and temperature can be fixed at other levels for the known and measured absorption spectra. During evacuation of a gaseous sample, the pneumatic system 112 cleans the previously provided gaseous sample from the ring-down cavity 84 and the various conduits for guiding gaseous samples from the thermal desorption tube 104 to the ring-down cavity 84.

The pneumatic system 112 has an intake portion that includes a nitrogen gas source 116. The nitrogen gas source 116 is a supply of very clean nitrogen gas that is pressurized or that can pressurize the nitrogen gas to at least above one atmosphere of pressure. In the present embodiment, the nitrogen gas source 116 is pressurized at five psi above ambient pressure, but can be varied as long as the compression is sufficient to pressurize the ring-down cavity 84 to one atmosphere, or some other selected atmospheric pressure at which the analyses are run. In the illustrated embodiment, the nitrogen gas source 116 is the nitrogen gas that evaporates off a liquid nitrogen reservoir. The nitrogen gas source 116 is connected via conduit 120 to a gas inlet valve 124a. An auxiliary gas inlet valve 124b enables connection of other gases, but is not regularly employed. The gas inlet and auxiliary gas inlet valves 124a, 124b are in communication with a gas intake line 120a. A pressure meter 128 is positioned along the gas intake line 120a, as well as a gas intake line valve 124c. A filter 130a is positioned along the gas intake line 120a in front of a cavity inlet valve 124d that seals the gas intake line 120a from the ring-down cavity 84. The filter 130a inhibits the entry of contaminants into the ring-down cavity 84 where they can deposit on the cavity mirrors 88 and interfere with reflection.

The gas inlet and auxiliary gas inlet valves 124a, 124b are in communication with a pathing valve 124e. The pathing valve 124e enables or disables direct access to a desorption tube line 120b and a sample outlet line 120c.

The desorption tube line 120b includes a forward valve 124f and a rearward valve 124g. The thermal desorption tube 104 is positioned between the forward valve 124f and the rearward valve 124g, with the receiving end 108 of the thermal desorption tube 104 being positioned towards the rearward valve 124g. The thermal desorption tube 104 is positioned within a heater 132.

The sample outlet line 120c includes a sample outlet valve 124h and a mass flow controller 136.

The pneumatic system 112 also has an outlet portion that includes a cavity outlet valve 124i in communication with the ring-down cavity 84. An outlet line 140 is in communication with the cavity outlet valve 124i. A pressure meter 144 is positioned along the outlet line 140. A vacuum cutoff valve 124j is positioned between the pressure meter 144 and a vacuum pump 148. A vacuum intake valve 124k is in communication with the vacuum pump 148 and draws air through a pump intake line 150. A filter 130b is positioned in the pump intake line 150 to inhibit entry of contaminants that can interfere with the working of the vacuum pump 148.

Valves 124a to 124k may be alternatively referred to herein as valves 124.

While the cavity inlet valve 124d and the cavity outlet valve 124i are shown for convenience coupled to the ring-down cavity 84 at certain locations, it will be understood that the locations at which the valves 124d, 124i are coupled to the ring-down cavity 84 may vary. In a preferred configuration, the cavity inlet valve 124d is in communication with the ring-down cavity 84 towards an end thereof adjacent the front cavity mirror 88a and the cavity outlet valve 124i is in communication with the ring-down cavity 84 towards an end thereof adjacent the rear cavity mirror 88b.

When a new gaseous sample is to be loaded into the ring-down cavity 84, the thermal desorption tube 104 containing the new gaseous sample is coupled to the pneumatic system 112 as shown.

During an evacuation phase, the vacuum intake valve 124k is opened and the vacuum pump 148 is turned on. The vacuum intake valve 124k is then closed, and the vacuum cutoff valve 124j, the cavity outlet valve 124i, the cavity inlet valve 124d, the gas intake line valve 124c, and the pathing valve 124e are opened in succession. The contents of the lines along this path and the ring-down cavity 84 are evacuated from the CRDS system 20 by the vacuum pump 148. The pressure meter 144 enables the determination of when the system has been evacuated sufficiently, especially when the pressure meter 128 is cut off from the vacuum pump 148. When it is determined that the system has been evacuated sufficiently, these same open valves 124j, 124i, 124d, 124c, and 124e are then closed in the reverse order. Thereafter, during a nitrogen fill phase, valves 124a, 124c, 124d, 124i, and 124j are opened to allow nitrogen gas from the nitrogen gas source 116 to fill the lines 120a and 140. The nitrogen gas is then purged using another evacuation phase. The nitrogen fill phase and the evacuation phase can be repeated as desired to clear out the lines. The CRDS system 20 is thus evacuated of the previously tested gaseous sample.

During the loading of the new sample, the thermal desorption tube 104 is flushed to remove carbon dioxide and water out of the thermal desorption tube 104 so that the amount of carbon dioxide and water loaded into the ring-down cavity 84 is minimized. In order to flush the thermal desorption tube 104, the gas intake valve 124a, the gas intake line valve 124c, and the rearward valve 124g are opened to give a path to the nitrogen gas to forward flush the thermal desorption tube 104. The thermal desorption tube 104 is selected to inhibit the collection of carbon dioxide and water with the gaseous sample, but there is still typically some carbon dioxide and water in the thermal desorption tube 104.

500 ml of nitrogen gas is put through the thermal desorption tube to get out carbon dioxide and water that have remained in the thermal desorption tube 104 from the original sample. Then the forward valve 124f and the sample outlet valve 124h are opened to provide a path to the mass flow controller 136. The mass flow controller 136 allows the nitrogen gas and borne carbon dioxide and water to be released at a specified flow rate. In the present configuration, this flow rate is 500 ml/min. All the valves 124 are then closed.

Once the carbon dioxide and the water have been removed from the thermal desorption tube 104, the pneumatic system 112 is evacuated again using the same process discussed above to remove the nitrogen gas just introduced in the pneumatic system 112 lines. The heater 132 surrounding the thermal desorption tube 104 then heats the thermal desorption tube 104 to the desired temperature to thermally desorb the new sample within the thermal desorption tube 104. The gas inlet valve 124a, the pathing valve 124e, the forward valve 124f, the rearward valve 124g, and the cavity inlet valve 124d are then opened to provide a direct path for the nitrogen gas from the nitrogen gas source 116, through the thermal desorption tube 104 having desorbed compounds of interest, and to the ring-down cavity 84.

It is desired to achieve a pressure of one atmosphere within the ring-down cavity 84 as all of the reference data collected and analyzed is at this pressure level, thereby ensuring that the results are repeatable.

The gas inlet valve 124a is toggled open and closed by the system, then the system waits for the pressure reading at the pressure meter 128 to stabilize and reach one atmosphere. If, upon stabilization of the pressure meter 128, the pressure reading is still below one atmosphere, the gas inlet valve 124a is toggled again to repeat the process until the pressure reading is one atmosphere. When the pressure meter 128 shows that the pressure level in the ring-down cavity 84 is one atmosphere, the valves are all closed.

If it is desired to desorb at multiple temperatures, the vacuum pump 148 is turned on, the cavity outlet valve 124i and the vacuum cutoff valve 124j are opened to evacuate the ring-down cavity 84. Then the cavity outlet valve 124i is closed before the desorption process is repeated.

A full evacuation is generally not performed between multiple desorptions as there is still some of the gaseous sample between the rearward valve 124g and the cavity inlet valve 124d that would be otherwise lost.

By pressurizing a fixed volume ring-down cavity containing the gaseous sample to a desired pressure level in this manner, the surface area within the ring-down cavity to which compounds can adhere can be decreased in comparison to variable volume ring-down cavities that may be used to raise the pressure within the cavity to the desired level.

Further, the pressure meter 128 is upstream from the path of the gaseous sample from the thermal desorption tube 104 to the ring-down cavity 84, thereby preventing its contamination by the sample.

Figure 2:
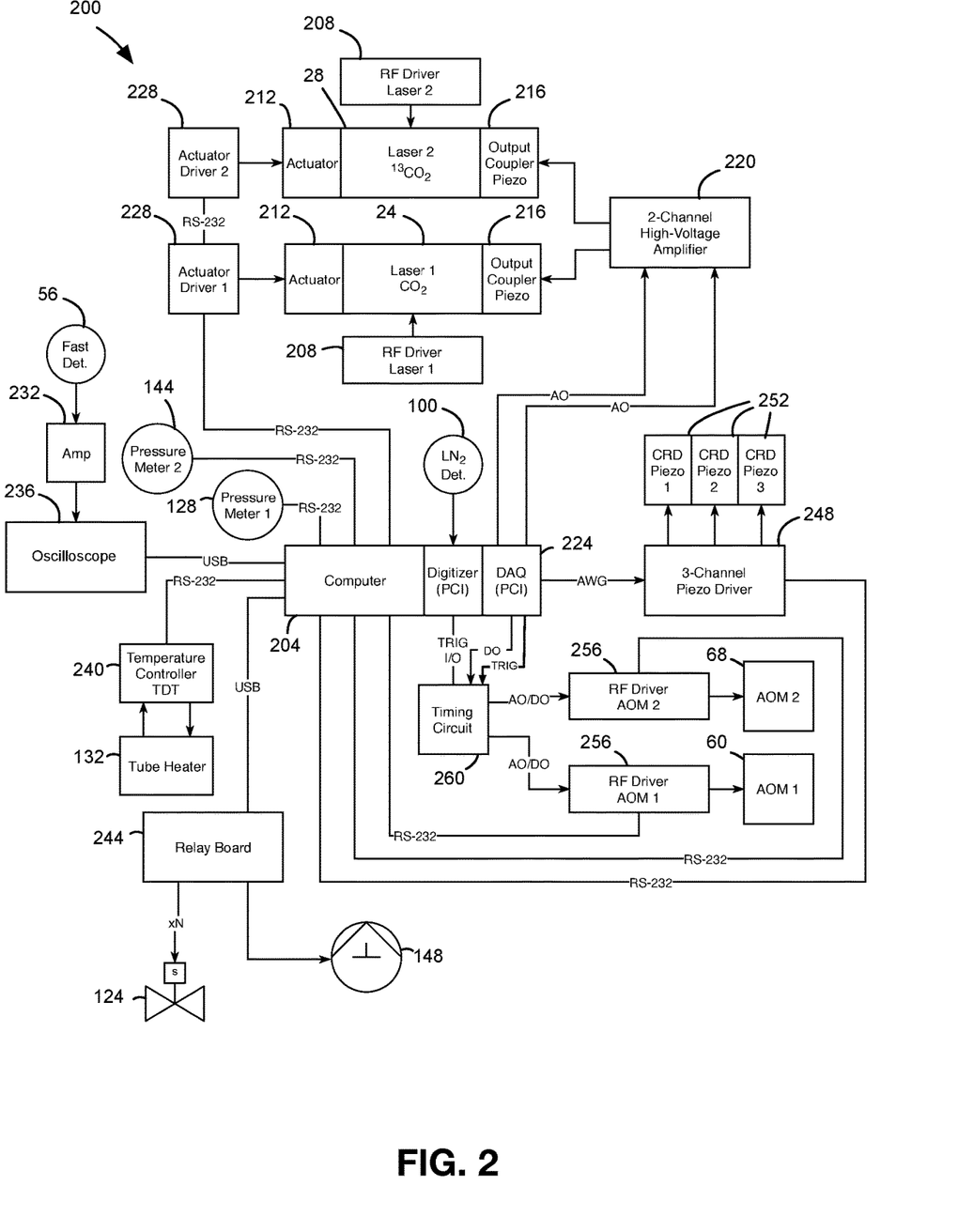
FIG. 2 is a schematic diagram of an electrical control system for controlling the various optical and pneumatic components of the cavity ring-down cavity ring-down system shown in FIG. 1.

FIG. 2 is a schematic diagram of an electronic control subsystem 200 for various components of the CRDS system 20 that are also illustrated. All of the lines represent electrical or electronic signals, with arrows representing unidirectional communications, setting of a voltage, etc., and lines that are not arrows representing bidirectional communications.

A computer 204 including one or more processors acts as a controller that controls the function of the various components illustrated in FIG. 1.

A pair of RF drivers 208 send 40 MHz signal to power the $CO_2$ laser 24 and the carbon-13 $O_2$ laser 28. Each of the lasers 24, 28 is tuned using an output coupler and an actuator 212. Each output coupler driven by a 1000V output coupler piezo 216. A two-channel high-voltage amplifier 220 that powers the output coupler piezos 216 is adjustable between 0V and 1000V. The high-voltage amplifier 220 is set with an analog output signal from a data acquisition ("DAQ") card 224 in the computer 204. The DAQ generates output between 0V and 10V, and the high-voltage amplifier 220 multiplies the signal by 100 to generate a signal of 0V to 1000V to power the output coupler piezo 216. Each actuator 212 that changes the angle for the grating is driven by an actuator driver 228 that is given instructions by the computer 204 via RS-232. Each actuator 212 is moved so many millimeters, which is translated into a pitch angle of the laser 24, 28.

Data signals from the pressure meters 132, 144 of the pneumatic system 112 are received through RS-232.

The fast detector 56 is connected to a small amplifier 232 and an oscilloscope 236 that can be used to read the amplitude and frequency of the beat signal that is used to tune the lasers 24, 28.

A temperature controller 240 for the thermal desorption tube heater 132 is controlled via RS-232 by the computer 204. The tube heater 132 includes a temperature sensor and a piece of aluminum that has heating tape wrapped around it. The heating tape and the temperature sensor are both connected to the temperature controller 240 which is a PID (proportional integral derivative) controller. The controller sets and reads back the temperature via RS-232 to the main computer 204.

A relay board 244 is connected to the computer 204 and is used to turn on and off all of the solenoid valves 124 and the vacuum pump 148.

A three-channel piezo driver 248 drives the piezo actuators 252 that actuate the micrometers 96b to adjust the length of the ring-down cavity 84. Each channel has two components: communications to the piezo driver through RS-232, and analog input from the DAQ card 224.

Each acousto-optic modulator 60, 68 is driven with an RF driver 256 that sends approximately a 40 MHz signal. Changing the frequency of the RF driver 256 changes the Bragg angle for a given optical wavelength, or changes the optical wavelength that a given or fixed Bragg angle is attuned to. If the RF driver 256 is tuned to a specific frequency and set to full power, most of the working beam 52 (about 85%) gets through. If adjusted to 80%, 70%, then the optical modulator 60, 68 will attenuate. If the RF driver 256 is set to zero, the optical modulator 60, 68 shuts off completely. The frequency of the RF driver is set through a component via RS232. An analog and digital component can set the amplitude and the on/off condition of the RF driver 256. In particular, the DAQ card 224 sends a signal to the timing circuit 260 which, in turn, generates the four necessary signals needed to enable and set the amplitude of the RF drivers. The timing circuit 260 can operate in a steady state condition or a ring-down triggering condition where the timing circuit 260 sets the four voltages to zero, and then returns to the previous voltage level after a pre-determined amount of time.

There is a digital output ("DO") from the DAQ card 224 that sets the timing circuit 260 to either a steady state or ring-down triggering mode. When in ring-down triggering mode, a trigger out from a digitizer 264 triggers the timing circuit 260 to set the RF driver voltages to 0. In steady state mode, the timing circuit 260 passes a trigger out (TRIG) from the DAQ card 224 to the digitizer 264 in order to synchronize cavity sweeps (through AWG) with the liquid nitrogen-cooled detector 100. That is, when the entire free spectral range of the ring-down cavity 84 is swept, the approximate voltage to set the cavity piezos to in order to resonate can be determined.

When it is desired to do a ring-down measurement, one of the lasers 24, 28 is tuned using the fast detector 56 and the oscilloscope 236. once the laser is tuned, the ring-down cavity is swept by sending a ramp signal generated by the DAQ card 224 to the piezo driver 248, and then the corresponding output beam intensity is measured on the liquid nitrogen-cooled detector 100. This provides a picture of where the resonant point is in the ring-down cavity 84 (e.g., 10V).

The piezo driver is set to 10V via RS-232, and a small 1V-2V amplitude sine wave is sent from the DAQ card 224, which also goes to the piezo driver 248. This results in a sine wave from 10-12V that goes to the piezo driver 248. The liquid nitrogen-cooled detector 100 will show sweeping back and forth over the resonance point in the ring-down cavity 84, and the center position is adjusted by RS-232 to move it higher or lower unit the time between sweeping forward and backward is equal. This is to tune the ring-down cavity 84 to the resonance point.

500 ring-downs are measured and the decay time which is used in the absorption coefficient calculation is calculated.

Once the gaseous sample is loaded in the ring-down cavity 84, one laser 24, 28 is tuned to a specific wavelength and its light is directed through the first optical modulator 60, reflected by the mirror 64, through the second optical modulator 68, and reflected by the mirror 72 to the ring-down chamber 80. The optical modulators 60, 68 attenuate the working beam 52 somewhat to modulate its intensity.

When the working beam 52 reaches the front cavity mirror 88a, a fraction, about 0.1%, penetrates the front cavity mirror 88a to enter the ring-down cavity 84. The majority of the working beam, about 99.9%, is initially reflected back along the same path to the working laser 24 or 28.

Initially, the ring-down cavity 84 is not illuminated. Light enters the ring-down cavity 84 and, as the majority of the light in the ring-down cavity 84 is reflected between the two cavity mirrors 88, the amount, or power, of light in the ring-down cavity 84 starts increasing as further light is introduced from outside via the working beam 52. A certain fraction of the light leaks out past the cavity mirrors 88. It takes a period of time to "fill" the ring-down cavity 84 with light. At that point, there is an equilibrium between the incoming light and the leakage. Once this equilibrium is achieved, the laser 24, 28 is extinguished or otherwise stopped from entering the ring-down cavity 84 via the optical modulators 60, 68.

When the ring-down cavity 84 is in resonance and approaches equilibrium (that is, the amount of light leaking out via the cavity mirrors 88 is equal to the amount of light entering from the working beam 52), there is destructive interference with the incoming laser light such that none or very little of the incoming laser light is reflected by the front cavity mirror 88a. As a result, once the ring-down cavity 84 is at equilibrium, reflection of the portion of the working beam 52 within the bandwidth of the ring-down cavity that is directed at the front cavity mirror 88a is substantially eliminated.

When the ring-down cavity is in equilibrium, a ring-down event can be started. The light entering the ring-down cavity 84 is extinguished as quickly as possible, and the infrared detector (that is, the liquid nitrogen-cooled detector 100) measures light intensity exiting the back end of the ring-down cavity 84 to determine exponential decay in the intensity of the light. It takes a certain amount of time for the light in the ring-down cavity 84 to ring down or decay. A decay constant (T) defined as the length of time for the intensity to drop to 1/e (equal to approximately 0.37) of the starting intensity or some other level can be measured and then compared to a baseline decay time without the sample to determine how much light is being absorbed by the gaseous sample. The acceleration in the ring down is attributed to the presence of the gaseous sample in the ring-down cavity 84. Using the measured decay times, an absorption coefficient can be calculated for the frequency/wavelength.

In order to extinguish the light entering the ring-down cavity 84, the computer 204 acts as a controller that directs the first optical modulator 60 to attenuate the light beam at or close to an attenuation limit of the first optical modulator 60 and to simultaneously direct the second optical modulator 68 to further attenuate the light beam at or close to an attenuation limit of the second optical modulator 68 to reduce an intensity of the light beam from the first optical modulator 60. In conventional CRDS systems, the light that is deflected by the single optical modulator drops off to zero over a short span of time. The additional light allowed to enter the ring-down cavity 84 can skew the spectroscopy results. It can therefore be desirable to have the laser light extinguished as quickly as possible.

In the CRDS system 20, by directing both optical modulators 60, 68 to shut off simultaneously, the amount of light deflected by the first optical modulator 60 during the short span of time is markedly reduced by the second optical modulator 68 as it is shutting down.

The second optical modular 68 greatly increases the attenuation achieved via the first optical modulator 60 alone. In the currently described embodiment, if the first optical modulator 60 can attenuate by 30 dB, and the second optical modulator 68 can attenuate by an additional 30 dB, with the total attenuation achieved via the optical modulators 60, 68 being the sum of their attenuation, or 60 dB. During filling of the ring-down cavity 84 with light, the optical modulators 60, 68 attenuate the working beam 52 to modulate its intensity. In the present configuration, each of the optical modulators 60, 68 attenuate the working beam 52 by 5 dB, for a total attenuation of 10 dB. As a result, each of the optical modulators 60, 68 can still further attenuate the working beam 52 by 25 dB for a total further attenuation of 50 dB during the extinguishing of the working beam 52. In a conventional setup, one optical modulator would have to attenuate a working beam by 10 dB, leaving 20 dB of further attenuation available for extinguishing the working beam. As will be understood, the working beam 52 can be extinguished much more rapidly via 50 dB of further attenuation via the two optical modulators 60, 68 than with one optical modulator with 20 dB of further attenuation. As a result, the amount of additional light introduced into the ring-down cavity 84 after the optical modulators 60, 68 have been directed to shut down is a small fraction of the light further introduced by a single optical modulator setup in a conventional CRDS system. By extinguishing the working beam 52 more quickly, the measured decay of light in the ring-down cavity 84 is less affected by the additional light during the ramp-down times of the optical modulators 60, 68, thus granting higher precision when matching the observed decay times against known decay times.

The process is repeated for lights of multiple frequencies to generate an absorption spectrum for the gaseous sample. For example, the light generated by the $CO_2$ laser 24 provides absorption coefficients for a range of frequencies. Similarly, absorption coefficients can be generated for a range of frequencies for the light from the carbon-13 $O_2$ laser 28. In this manner, an absorption spectrum can be developed for the sample.

While, in the above-described embodiment, the light sources are two lasers that produce light in the mid-infrared range, it will be appreciated that other light sources can be employed. For example, a laser producing light in the visible spectrum or a near-infrared laser can be employed. Further, in some scenarios, the CRDS system can include only one laser, or three or more lasers, to generate the working beam.

Electro-optic modulators can be used in place of acousto-optic modulators.

The acousto-optic modulators can be configured so that the frequency of the working beam is shifted up or down. As long as the net frequency shift effected by the acousto-optic modulators shifts the frequency of the working beam significantly away from the frequency of the working beam being generated by the laser(s) so that the reflected light is outside of the bandwidth of the laser light being generated, the amount of interference between the reflected light and the generated working beam can be minimized.

In other embodiments, more than two optical modulators can be employed in a CRDS system to provide further extinguishing capacity to more quickly extinguish the working beam at the commencement of a ring-down event.

One or more focusing lenses can be employed in other embodiments to mode match the ring-down cavity.

Analysis of the gaseous samples can be performed at pressure levels other than one atmosphere in other embodiments. The breadth of the absorption spectrum may change accordingly.

Although specific advantages have been enumerated above, various embodiments may include some, none, or all of the enumerated advantages.

Persons skilled in the art will appreciate that there are yet more alternative implementations and modifications possible, and that the above examples are only illustrations of one or more implementations. The scope, therefore, is only to be limited by the claims appended hereto.

LIST OF REFERENCE NUMERALS

20 CRDS system
24 $CO_2$ laser
28 carbon-13 $O_2$ laser
32 first laser beam
36 second laser beam
40 mirror
44 beam splitter
48 sampling beam
52 output beam
56 fast detector
60 first optical modulator
64 mirror
68 second optical modulator
72 focusing lens
76 mirror
80 ring-down chamber
84 ring-down cavity
88 cavity mirror
88a front cavity mirror
88b rear cavity mirror
92 mirror mounts
96 micrometer
100 liquid nitrogen-cooled detector
104 thermal desorption tube
108 receiving end
112 pneumatic system
116 nitrogen gas source
120 conduit
120a gas intake line
120b desorption tube line
120c sample outlet line
124 solenoid valve
124a gas inlet valve
124b auxiliary gas inlet valve
124c gas intake line valve
124d cavity inlet valve
124e pathing valve
124f forward valve
124g rearward valve
124h cavity outlet valve
124i sample outlet valve
124j vacuum cutoff valve
124k vacuum intake valve
128 pressure meter
130a, 130b filter
132 heater
136 mass flow controller
140 outlet line
144 pressure meter
148 vacuum pump
200 electronic control subsystem
204 computer
208 RF driver
212 actuator
216 output coupler piezo
220 high-voltage amplifier
224 DAQ card
228 actuator driver
232 amplifier 236 oscilloscope
240 temperature controller
244 relay board
248 three-channel piezo driver
252 piezo actuator
256 RF driver
260 timing circuit
264 digitizer

What is claimed is:

1. A cavity ring-down spectroscopy system, comprising:
 at least one laser that generates a light beam;
 a first optical modulator positioned to attenuate the light beam from the at least one laser;
 a second optical modulator positioned to attenuate the light beam from the first optical modulator;
 a ring-down cavity positioned to receive the light beam from the second optical modulator;
 a controller connected to the first optical modulator and the second optical modulator to direct the first optical modulator to attenuate the light beam by about 99.9% and to simultaneously direct the second optical modulator to further attenuate the light beam by about 99.9% to reduce or extinguish an intensity of the light beam from the first optical modulator; and
 at least one light sensor to measure an intensity of light leaked from the ring-down cavity.

2. The cavity ring-down spectroscopy system of claim 1, further comprising at least one focusing lens for focusing the light beam to match an optical mode of the ring-down cavity.

3. The cavity ring-down spectroscopy system of claim 1, wherein each of the first and second optical modulators is an acousto-optic modulator or an electro-optic modulator.

4. A method of modulating a light beam in a cavity ring-down spectroscopy system, comprising:
 generating a light beam via at least one laser;
 receiving the light beam in a ring-down cavity;
 attenuating the light beam from the at least one laser via a first optical modulator by about 99.9%;
 attenuating the light beam from the first optical modulator via a second optical modulator by about 99.9%;
 measuring a rate of decay of light leaked from the ring-down cavity.

5. The method of claim 4, wherein the first and second optical modulators are acousto-optic modulators or electro-optic modulators.

6. The method of claim 4, wherein the first optical modulator and the second optical modulator are simultaneously directed to attenuate the light beam travelling towards the ring-down cavity to reduce or extinguish an intensity of the light beam.

* * * * *